United States Patent [19]

Suzuki

[11] Patent Number: 4,651,966
[45] Date of Patent: Mar. 24, 1987

[54] BRACKET FOR SUPPORTING UNIVERSAL ARM OF DENTAL X-RAY APPARATUS

[75] Inventor: Shouzou Suzuki, Kashiwa, Japan

[73] Assignee: Kabushiki-Kaishi Tokyo Emix, Saitama, Japan

[21] Appl. No.: 830,751

[22] Filed: Feb. 19, 1986

[51] Int. Cl.$^4$ ............................................. F16M 3/00
[52] U.S. Cl. ..................................... 248/674; 248/282
[58] Field of Search ............. 248/674, 585, 476, 122, 248/282, 289.1, 283, 296, 291, 314, 324

[56] References Cited

U.S. PATENT DOCUMENTS

| | | | |
|---|---|---|---|
| 4,003,536 | 1/1977 | Sekerich | 248/585 |
| 4,413,868 | 11/1983 | Gorkiewicz | 248/282 X |
| 4,487,389 | 12/1984 | Ziegler | 248/282 |
| 4,500,063 | 2/1985 | Schmidt et al. | 248/314 X |

Primary Examiner—Ramon O. Ramirez
Attorney, Agent, or Firm—Sandler & Greenblum

[57] ABSTRACT

A bracket for supporting a universal arm of a dental X-ray apparatus having a construction in which: the bracket is provided with at least one of a clearance hole in which a setscrew is loosely inserted, which clearance hole crosses a pair of opposite adjust-screw holes which are connected in series with each other, which adjust-screw holes are threadably engaged with a pair of adjust screws, so that, when the adjust screws are rotated in the adjust-screw holes to be moved forward and rearward while abutting against the setscrew in the clearance hole, the bracket is moved to a desired position to make it possible that the bracket takes a desirable mounting condition.

1 Claim, 4 Drawing Figures

BRACKET FOR SUPPORTING UNIVERSAL ARM OF DENTAL X-RAY APPARATUS

BACKGROUND OF THE INVENTION

1. Field of the Invention

The present invention relates to a bracket for vertically supporting a base portion of a universal arm which supports a X-ray generator of a X-ray apparatus.

2. Description of the Prior Art

In general, an arm for freely moving the X-ray generator is pivotally supported by a bracket provided in a side wall of a X-ray examination room. In such case, when the bracket is not adequately mounted on the side wall of the X-ray examination room so that a longitudinal axis hole of the bracket for pivotally supporting the arm is not hald vertically, the whole arm is inclined so that the X-ray generator is impaired in its accurate movement. However, it is difficult to accurately mount the bracket in a vertical condition. Consequently, hitherto, mounting operation of the bracket is performed by using a process of trial and error so that it is troublesome and takes much time to mount the bracket accurately. These are defects inherent in the prior art.

SUMMARY OF THE INVENTION

In order to eliminate the above defects, it is an object of the present invention to provide a bracket for vertically supporting a base portion of a universal arm which supports a X-ray generator of a dental X-ray apparatus, which bracket may be mounted on such a side wall of the X-ray examination room with a high accuracy in its verticality according to a process in which the bracket is first temporarily mounted on the side wall to make it possible that a mounting condition of the bracket is easily adjusted through adjustment of its adjust screw speedily.

DESCRIPTION OF THE PREFERRED EMBODIMENT

Figure 1:
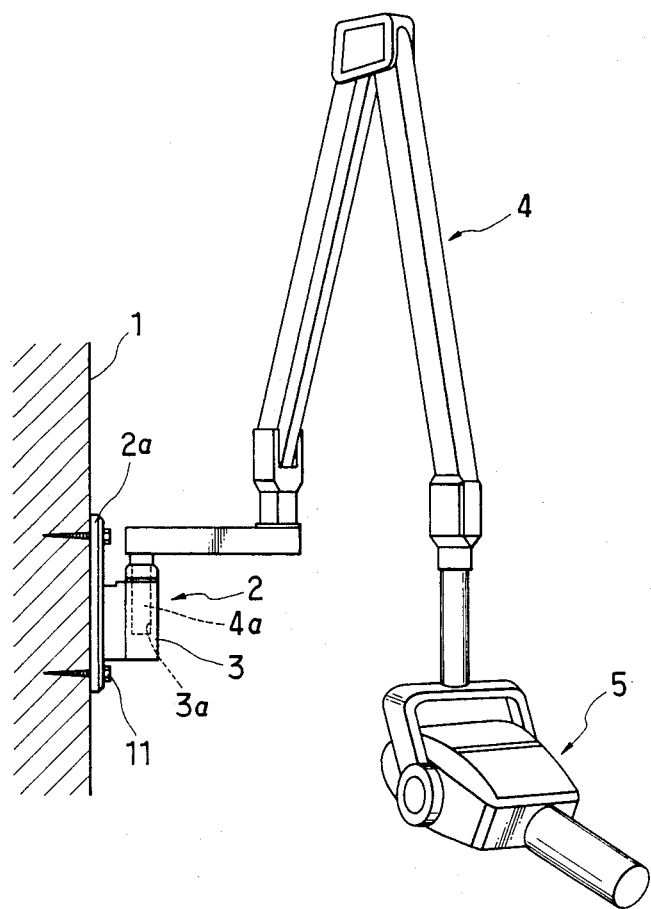
FIG. 1 is a perspective view of a dental X-ray apparatus to which a universal arm is mounted through the bracket of the present invention.

In the drawings: the reference numeral 1 designates a side wall; the numeral 2 designates a bracket; the numeral 2a designates a bracket base plate; the numeral 6 designates a mounting hole; the numeral 7 designates a clearance hole; the numeral 8 designates a reference hole; the numeral 9 designates a mounting hole; the numerals 10 to 13 designate wood screws; the numerals 14a and 14b designate adjust screw holes; and the numerals 16a and 16b designate adjust screws.

In FIG. 1, there is shown a dental X-ray apparatus mounted on a shield wall.

In FIG. 1, the reference numeral 1 designates the side wall of a X-ray examination room, on which is mounted a bracket 2 which is provided with a base plate 2a in which is formed a vertical boss 3 having a longitudinal hole 3a in which is inserted a base portion vertical shaft 4a of a universal arm 4 on a free end of which a X-ray generator 5 is mounted.

Figure 2:
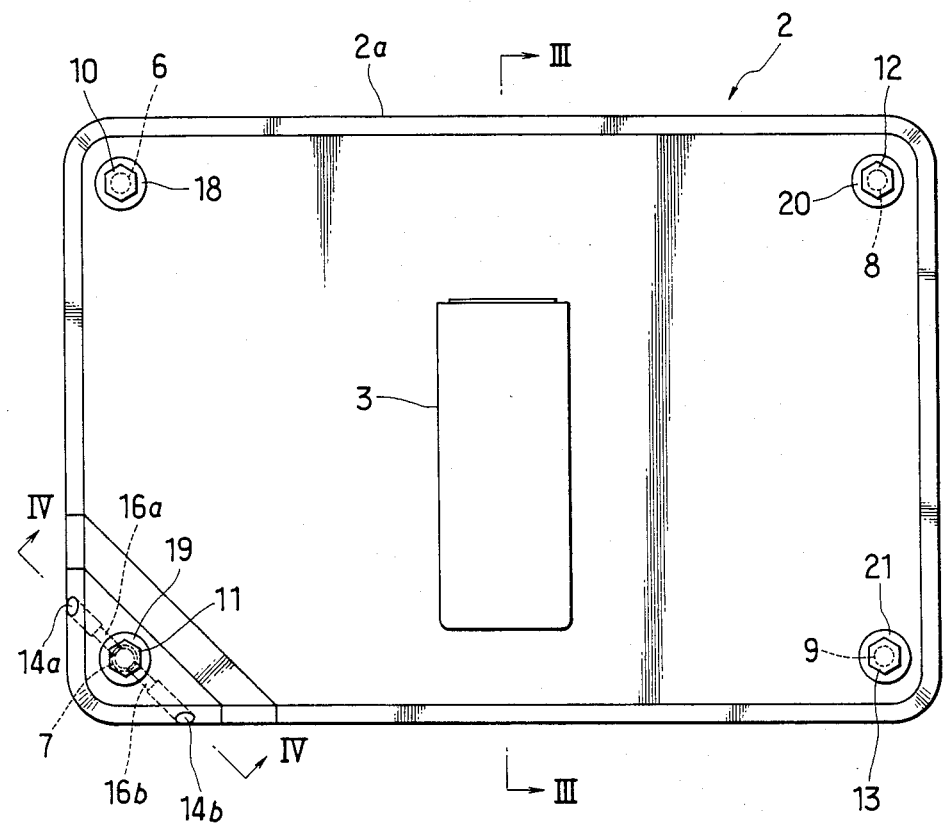
FIG. 2 is a front view of the bracket of the present invention.
Figure 3:
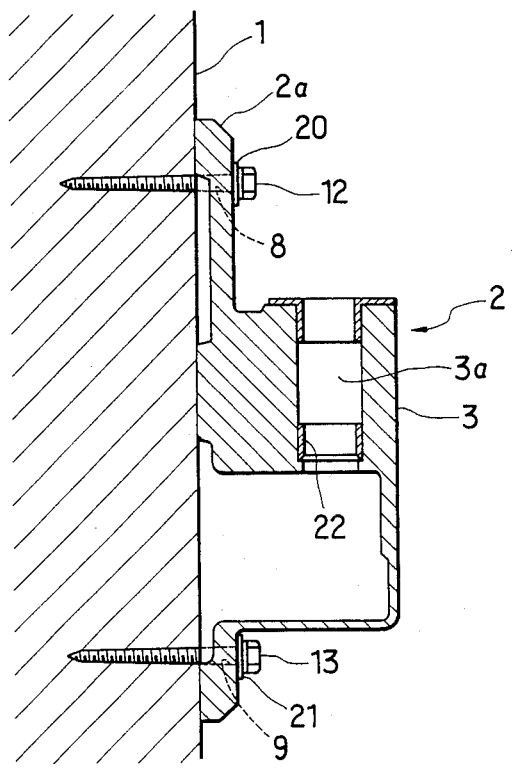
FIG. 3 is a longitudinal sectional view taken along the line 111—111 of FIG. 2.
Figure 4:
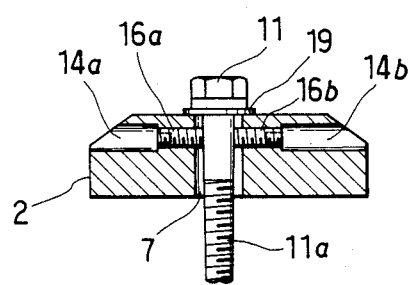
FIG. 4 is an enlarged sectional view taken along the line 1V—1V of FIG. 2.

In FIGS. 2 to 4, the bracket 2 is shown in detail, in which, the mounting holes 6 to 9 for receiving setscrews are provided in four corners of the bracket base plate 2a of the bracket 2. Among these mounting holes 6 to 9, a mounting hole 8 positioned in one of corners in an upper edge portion of the bracket base plate 2a acts as a reference hole 8, and only another mounting hole 7 which is positioned on a diagonal line of the bracket 2 passing through the mounting hole 8 thereof and also positioned in one of corners in a lower edge portion of the bracket base plate 2a thereof acts as a clearance hole 7 a diameter of which is slightly larger than a diameter of a threaded portion of a wood screw 11 which acts as a setscrew 11. In a portion of the bracket base plate 2a in which portion the clearance hole 7 is provided, there are provided a pair of adjust-screw holes 14a, 14b in series so that a mutual longitudinal axis of these adjust-screw holes 14a, 14b crosses the above-mentioned diagonal line of the bracket 2 at right angles, with which adjust-screw holes 14a and 14b are threadably engaged adjust screws 16a and 16b respectively to make it possible that the adjust screws 16a, 16b are rotated in their normal and reverse directions with the use of a suitable screwdriver such as Allen wrench and the like.

Incidentally, the reference numerals 18 to 21 designate plain washers; and the numeral 22 designates a bearing for pivotally supporting the base portion vertical shaft 4a of the universal arm 4.

The bracket 2 having the above-mentioned construction is mounted on the side wall 1 of the X-ray examination room in the following manner.

At first, wood screws 12 and 11 are screwed into the reference hole 8 and the clearance hole 7 of the bracket base plate 2a respectively so that the bracket base plate 2a is temporarily attached to the side wall 1 of the X-ray examination room.

Then, a spirit level (not shown) is placed on an upper end surface of the vertical boss 3 of the bracket 2 to detect a deviation angle of a longitudinal axis of the hole 3a of the vertical boss 3 from a vertical line by inspecting a horizontality of the upper end surface of the vertical boss 3, so that, in this temporal attaching condition of the bracket 2, the adjust screws 16a, 16b are rotated in their normal and reverse directions as required with the use of a suitable screwdriver such as Allen wrench and the like to be moved forward and rearward in the adjust-screw holes 14a, 14b to make it possible that the bracket base plate 2a is swung around the reference hole 8 until the spirit level indicates a horizontal state of the upper end surface of the vertical boss 3 of the bracket 2 in which horizontal state the longitudinal axis of the hole 3a of the vertical boss 3 is held vertical. Consequently, in this horizontal state of the upper end surface of the vertical boss 3 of the bracket 2, the wood screws 12 and 11 having been screwed into the reference hole 8 and the clearance hole 7 respectively are finally fastened while other wood screws 10 and 13 are also screwed into the remaining mounting holes 6 and 9 of the bracket 2 respectively to be fastened, whereby the bracket 2 may be mounted on the side wall 1 of the X-ray examination room in a condition in which the longitudinal axis of the hole 3a of the vertical boss 3 of the bracket 2 is kept vertical.

As described above, according to the present invention, it is possible to mount the bracket 2 for supporting the universal arm 4 of the dental X-ray apparatus on the side wall 1 of the X-ray examination room in a condition in which the longitudinal axis of the hole 3a of the vertical boss 3 of the bracket 2 is kept vertical, while a procedure for determine a verticality of the longitudinal axis of the hole 3a of such vertical boss 3 may be proceeded easily and speedily with a very high accuracy so that it is possible to ensure a precise action of the X-ray generator of the X-ray apparatus in its use.

What is claimed is:

1. A bracket for supporting a universal arm of a dental X-ray apparatus having a construction in which:

a longitudinal axis hole in which a base portion vertical shaft of said universal arm is inserted is formed in a boss which is provided in a front surface of a bracket base plate of said bracket in projecting manner;

a plurality of mounting holes for receiving screws are formed in four corners of said bracket base plate, one of which mounting holes acts as a reference hole, another of which mounting holes acts as a clearance hole which is positioned on a diagonal line of said bracket base plate, which diagonal line passes through said reference hole, a diameter of which clearance hole is slightly larger than that of said screw acting as a setscrew;

a pair of adjust-screw holes are formed in series in a portion of said bracket base plate of said bracket (2) in which portion said clearance hole is formed, so that a mutual longitudinal axis of said pair of said adjust-screw holes crosses said diagonal line passing through said reference hole and said clearance hole and also crosses said clearance hole (7), and a pair of adjust screws (14a, 14b) are threadably engaged in said pair of (16a, 16b).

* * * * *

UNITED STATES PATENT AND TRADEMARK OFFICE
CERTIFICATE OF CORRECTION

PATENT NO. : 4,651,966
DATED : March 24, 1987
INVENTOR(S) : Shouzou Suzuki

It is certified that error appears in the above-identified patent and that said Letters Patent is hereby corrected as shown below:

Column 1, line 9, (both appearances), column 1, line 13, column 1, line 31 and column 1, line 65, "a" should read -- an --.

Column 1, line 46, "line 111-111" should read -- line III-III --

Column 1, line 49, "line 1V-1V" should read -- line IV-IV --

Column 2, line 1, "a" should read -- an --.

Signed and Sealed this

First Day of March, 1988

Attest:

DONALD J. QUIGG

*Attesting Officer*  *Commissioner of Patents and Trademarks*